(12) United States Patent
Rath et al.

(10) Patent No.: US 10,238,619 B1
(45) Date of Patent: Mar. 26, 2019

(54) COMPOSITION AND METHOD OF USING THE SAME

(71) Applicants: Matthias W Rath, Aptos, CA (US); Aleksandra Niedzwiecki, Aptos, CA (US); Anna Goc, Sanjose, CA (US)

(72) Inventors: Matthias W Rath, Aptos, CA (US); Aleksandra Niedzwiecki, Aptos, CA (US); Anna Goc, Sanjose, CA (US)

(73) Assignee: Matthias W. Rath, Aptos, CA (US)

( * ) Notice: Subject to any disclaimer, the term of this patent is extended or adjusted under 35 U.S.C. 154(b) by 0 days.

(21) Appl. No.: 15/799,573

(22) Filed: Oct. 31, 2017

(51) Int. Cl.
*A61K 31/20* (2006.01)
*A61K 31/122* (2006.01)
*A61K 31/11* (2006.01)
*A61K 31/05* (2006.01)

(52) U.S. Cl.
CPC .............. *A61K 31/20* (2013.01); *A61K 31/05* (2013.01); *A61K 31/11* (2013.01); *A61K 31/122* (2013.01)

(58) Field of Classification Search
CPC ...................................................... A61K 31/20
See application file for complete search history.

(56) References Cited

U.S. PATENT DOCUMENTS 9,743,675 B2 * 8/2017 De Leij .................. A01N 35/04

OTHER PUBLICATIONS

Goc et al. Journal of applied microbiology, 2015, 119(6):1561-72.*
Pauli et al., International Journal of Aromatherapy, 2001, 11 (3):126-133.*
Nuernberg et al. CAS: 1985-49151, 1985.*
Rath et al. Therapeutic Advance in Infectious Disease, 2016, 3(3-4):75-82.*
Todars Online Text book of Bacteriology, http://textbookofbacteriology.net/Lyme.html.
Radhey S. Gupta, Origin of diderm (Gram Positive) bacteria: Antibiotic selection pressure rather then endosymbiosis likely led to the evolution of bacterial cells with two membranes, Antonie van Leeuwenhoek (2011) 100:171-182.
Borrelia Burgdorferi, Wikipedia, Jul. 15, 2016.

* cited by examiner

*Primary Examiner* — Rei Tsang Shiao
(74) *Attorney, Agent, or Firm* — Geeta Kadambi; Riddhi IP LLC

(57) ABSTRACT

A composition of a fatty acids, essential oils, plant extracts, phenols, and terpenoids and used for treating Lyme disease is disclosed. Compositions as a mix of ingredients was tested in various combinations and concentration against active (spirochetes), as well as persistent/latent forms, (knob-shaped/rounded-forms) and biofilm of the bacteria, i.e., *Borrelia burgdorferi* and *Borrelia garinii*. The results document pleiotropic effects of the tested combinations against all tested forms of *Borrelia* sp. and show their better efficacy than doxycycline—the current antibiotic treatment against Lyme disease.

16 Claims, 16 Drawing Sheets

COMPOSITION AND METHOD OF USING THE SAME

FIELD OF TECHNOLOGY

This disclosure relates generally to novel composition and method of using them for treating bacterial disease.

BACKGROUND

Lyme disease (LD) is the most common tick-borne illness today in Europe and North America (Anderson et al. 1983, Burgdorfer et al. 1982, Johnson et al. 2014, Dryden et al. 2010). The Center for Disease Control (CDC) states that there may be more than 300,000 cases and as high as one million cases per year in United States alone (Stricker et al. 2014). This publication further states that Lyme disease is approaching an epidemic proportion and the monotherapy of using antibiotics may not be sufficient. Chronic/persistent Lyme disease involves latent forms such as rounded bodies and biofilm formation (Stricher et al. 2011).

Bacteria from genus *Borrelia* are pathogenic mico-aerophilic and slow-growing pathogens known for their persistency (Embers et al. 2012, Sapi et al. 2011, Hodzic et al. 2014, Stanek et al. 2012, Hodzic et al. 2008, Stricker et al. 2013, Barthold et al. 2010). Out of 36 currently recognized species, 17 of them are either acknowledged or suspected to cause LD. They are known as *Borrelia burgdorferi* sensu lato and include species such as *Borrelia burgdorferi* sensu stricto (predominantly causing this illness in North America) as well as *Borrelia afzelii* and *Borrelia garinii* (predominantly causing this illness in Europe) (Lovrich et al. 1994). The vegetative form of *Borrelia* sp. are spirochetes that are motile and can survive viscous conditions in human and animal blood, and as well they are capable of entering their cells (Miller et al. 2014, Zhao et al. 2014, Wu et al. 2011, Coleman et al. 1995). When hostile conditions are introduced these bacteria can adopt different latent persistent forms such as knob-shaped/rounded bodies (cysts, granular forms, L-forms) and aggregates (biofilm-like structures) both in vitro and in vivo (Gruntar et al. 2001, Brorson et al. 1998, Krause et al. 2006). Especially the ability of *Borrelia burgdorferi* sensu lato to convert and re-convert to cystic form was observed, which may be one of the reasons why this infection can sometimes become persistent and/or re-surface after being silent for a long time (Krause et al. 2006, Brorson et al. 1997, Donta 2002). Moreover, genomic analysis revealed that *Borrelia burgdorferi* sensu lato has a gene for efflux mechanism. This might be responsible for developing antibiotic resistance, although more in depth studies are warranted to prove such hypothesis (Fraser et al. 1997).

Based on diagnostic test results, the most recent estimates indicate that the number of LD cases in just the United States reaches 300,000 each year; however, there might be unreported cases that are not reflected in the statistics (Johnson et al. 2014, Krause et al. 2006, Stricker et al. 2014 Meek et al. 1996). This has made this disease the most common vector-born disease in the Northern Hemisphere (Johnson et al. 2014, Dryden et al. 2010, Krause et al. 2006). Currently, the frontline treatment for LD is based on antibiotics. Lactams and tetracyclines are the most frequently applied and include doxycycline, amoxicillin, and cefuroxime axetil. Macrolides, such as azithromycin, clarithromycin, and erythromycin, are the second class and appear to be less effective than lactams (Shapiro 2014).

Currently one of the most often prescribed antibiotics against *Borrelia burgdorferi* sensu lato infection is doxycycline (Shapiro 2014, Cameron et al. 2014, Nadelman et al. 2001, Wormser et al. 2006, Mygland et al. 2010). Its use began in the late sixties last century against infections other than LD (Li et al. 2013, Nelson et al. 2011). Since then, the application of doxycycline extended and has been on the World Health Organization's List of Essential Medicines as one of the most important medications needed in a basic health system (Nelson et al. 2011, World Health Organization 2015). Doxycycline is a broad-spectrum antibiotic belonging to the class of tetracyclines. Like other agents in this class, it is an anti-bacterial and anti-parasite agent targeting protein production in general (Nelson et al. 2011, World Health Organization 2015), The American Society of Health-System Pharmacists 2015). Its side effects are similar to those of other members of this antibiotic class, including the development of an erythematous rash after exposure to sun. Moreover, doxycycline is classified as a class D drug and is thus restricted for administration to pregnant women and children under the age of eight (Mylonas 2011). Although, doxycycline is one of the most frequently prescribed antibiotics, especially for the early stages of LD, its continued treatment is not recommended since the long-term effectiveness has not been proven (Stanek et al. 2012, Delong et al. 2012). In vitro studies revealed that doxycycline is effective against active (vegetative) form of *Borrelia* sp., with moderate action against their biofilms, and ineffective against the latent knob-shaped/rounded forms (Sapi et al. 2011, Baradaran-Dilmaghani et al. 1996). Observed persistency and/or relapse of LD symptoms in the absence of ongoing antibiotic treatment were observed as well (Krause et al. 2006, Donta 2002, Klempner et al. 2001). This would suggest that doxycycline may either facilitate generation of latent forms or is inefficient in their elimination (Hodzic et al. 2008, Gruntar et al. 2001, Oksi et al. 1999, Straubinger et al. 1997, Straubinger 2000).

Antimicrobials derived from natural sources such as plants, herbs, and fruits, and essential oils, have shown activity against a plethora of bacteria and fungi, but are poorly explored against *Borrelia* sp. (Morrison et al. 2014, Takeuchi et al. 2014, Zhang et al. 2013). Despite a rather small pool of available data on this subject, Bronson and Bronson study exhibited grapefruit seed extract as a powerful in vitro agent against spirochetes and their cystic forms of *Borrelia burgdorferi* sensu lato (Brorson et al. 2007). *Dipsacus sylvestris* extract against *Borrelia burgdorferi* sensu stricto revealed growth inhibiting activity as well (Liebold et al. 2011), whereas Sapi et al., reported significant efficacy of leaf extracts from *Stevia Rebaudiana* on all forms of *Borrelia burgdorferi* (Theophilus et al. 2015).

Natural components tested against *Borrelia* sp. were limited to individual compounds or extracts isolated from a specific plant species. There is a need for new and improved treatments against *Borrelia* sp.

SUMMARY

Several compositions and efficacy of treating several forms of bacterial infection are discussed in this disclosure. The instant application describes a novel composition and use of novel composition in the treatment and/or prevention of Lyme disease caused by *Borrelia* sp. The novel composition comprises of fatty acids, essential oils, plant extracts, phenols, and terpenoids in various combinations. In another embodiment, the novel composition consists of fatty acids, essential oils, plant extracts, phenols, and terpenoids in various combinations. The novel composition is effective against both the active (spirochetes) and dormant/latent persistent (knob/rounded-shaped bodies, biofilm) forms of *Borrelia* sp. In one embodiment a treatment/prevention for Lyme disease is being disclosed. In another embodiment, a novel composition for treating/preventing Lyme disease is disclosed. In another embodiment, knob/rounded-shaped forms (persisters), spirochetes, and biofilm are treated using the novel composition. In another embodiment, two species of Lyme disease bacteria and their various forms are treated by the novel composition. Once the mixture is administered the infected mammal is treated simultaneously for all forms, such as persistent forms (knob/rounded-shaped forms), biofilm, and active/spirochete forms of *Borrelia* sp.

In one embodiment, the composition comprises of a fatty acid between 0.075-0.1 mg/ml, essential oil in the range of 0.075-0.1 mg/ml, plant extract in the range of 0.075-0.1 mg/ml and terpenoids in the range of 0.75-0.1 mg/ml All the composition ingredients are grouped in different combinations composed of 3 to 4 ingredients so in total they comprise 0.3 mg/ml of the entire treatment portion of the mixture.

In one embodiment, a composition of clove oil (0.075 mg/ml), lemongrass oil (0.075 mg/ml), spearmint oil (0.075 mg/ml) or cinnamon oil (0.075 mg/ml) and linoleic acid (0.075 mg/ml) are used as a composition (Mix 1) to treat active spirochete form of *Borrelia burgdorferi* and *Borrelia garinii* in mammals.

In one embodiment, linoleic acid (0.075 mg/ml), eugenol (0.075 mg/ml citral (0.075 mg/ml) R-carvone (0.075 mg/ml or cinnamon are used as a composition (Mix 2) to treat active spirochete form of *Borrelia burgdorferi* and *Borrelia garinii* in mammals.

In one embodiment, time-dependent evaluation of the anti-borreliae effect of tested composition mixes against persistent (rounded) form of *Borrelia burgdorferi* and *Borrelia garinii* was determined by SYTO9/IP assay staining. Tested composition mixes according to the invention contained: Mix 1: clove oil (0.075 mg/ml) lemongrass oil (0.075 mg/ml) spearmint oil (0.075 mg/ml) or cinnamon oil (0.075 mg/ml) and linoleic acid (0.075 mg/ml). In another composition, Mix 2: eugenol (0.075 mg/ml), citral (0.075 mg/ml), linoleic acid (0.075 mg/ml), and R-carvone or cinnamon oil (0.075 mg/ml). In another embodiment the final concentration for each component of Mix 1 and Mix 2 assembled in sets of three were 0.3 mg/ml. Final concentration of all ingredients in any particular combination of the Mixes was 0.3 mg/ml.

In another embodiment, Live/Dead ratio of rounded forms evaluated after 72 hours post-treatment with tested individual compounds against persistent (rounded) form of *Borrelia burgdorferi* and *Borrelia garinii* was determined by SYTO9/IP assay staining. The components for the test included: clove oil (0.075-0.3 mg/ml), lemongrass oil (0.075-0.3 mg/ml spearmint oil (0.075-0.3 mg/ml) or cinnamon oil (0.075-0.3 mg/ml linoleic acid (0.075-0.3 mg/ml), eugenol (0.075-0.3 mg/ml), citral (0.075-0.3 mg/ml), R-carvone (0.075-0.3 mg/ml).

In another embodiment, Live/Dead ratio of rounded forms evaluated after 72 hours post-treatment with mixtures according to the invention (Mixes 1 and 2) against persistent (rounded) form of *Borrelia burgdorferi* and *Borrelia garinii* determined by SYTO9/IP assay staining. Tested mixes contained: Mix 1: clove oil (0.075 mg/ml), lemongrass oil (0.075 mg/ml), spearmint oil (0.075 mg/ml) or cinnamon oil (0.075 mg/ml), linoleic acid (0.075 mg/ml), and Mix 2: eugenol (0.075 mg/ml), citral (0.075 mg/ml), linoleic acid (0.075 mg/ml), R-carvone (0.075 mg/ml) or cinnamon oil (0.075 mg/ml); and were compared with control (0.3 mg/ml) ethanol.

In another embodiment, evaluation of the anti-*borrelia* effect of tested mixes against persistent (biofilm) form of *Borrelia burgdorferi* and *Borrelia garinii* determined by SYTO9/IP assay staining. Tested mixes (1-2) contained: Mix 1: clove oil (0.075 mg/ml), lemongrass oil (0.075 mg/ml), spearmint oil (0.075 mg/ml) or cinnamon oil (0.075 mg/ml), linoleic acid (0.075 mg/ml), and Mix 2: eugenol (0.075 mg/ml), citral (0.075 mg/ml), linoleic acid (0.075 mg/ml), R-carvone (0.075 mg/ml) or cinnamon oil (0.075 mg/ml); and were compared with control (0.3 mg/ml) ethanol.

Individual ingredients (clove oil, lemongrass oil, spearmint oil, cinnamon oil, linoleic acid, eugenol, citral, R-carvone) tested at 0.075 mg/ml concentrations each showed lower efficacy against biofilm than their combinations at respective concentrations used in mixes (Mix 1 and Mix 2)

Other features will be apparent from the accompanying drawings and from the detailed description that follows.

BRIEF DESCRIPTION OF DRAWINGS

Example embodiments are illustrated by way of example and not limitation in the figures of the accompanying drawings, in which like references indicate similar elements and in which:

Figures 13C, 13D:
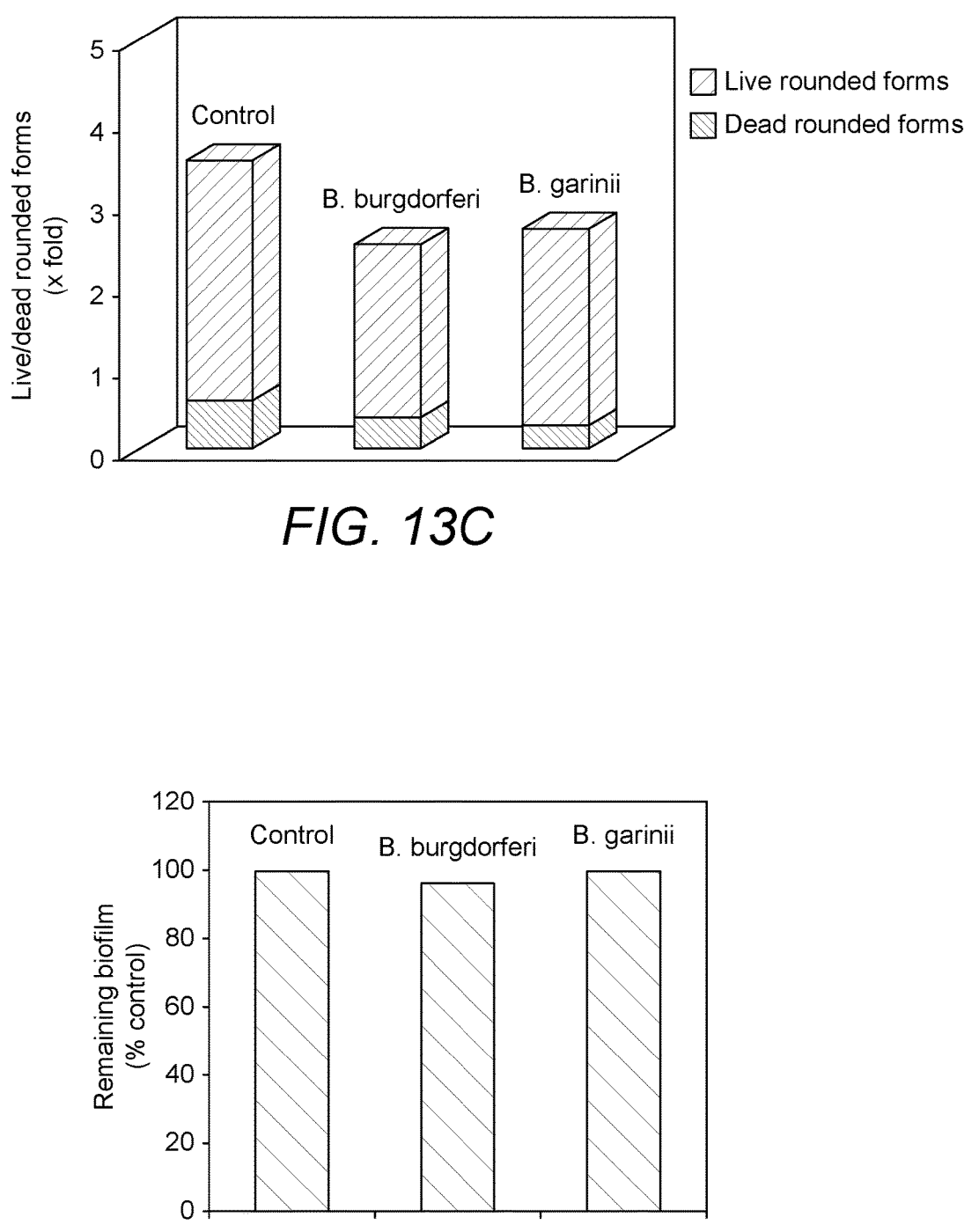

FIGS. 13A, 13B, 13C and 13D: Evaluation of the anti-borreliae effect of doxycycline against active (spirochete) and persistent forms (rounded forms, biofilm) of *Borrelia burgdorferi* and *Borrelia garinii* determined by SYTO9/IP staining; doxycycline (0.3 mg/ml), control (0.3 mg/ml ethanol).

Figure 1A:
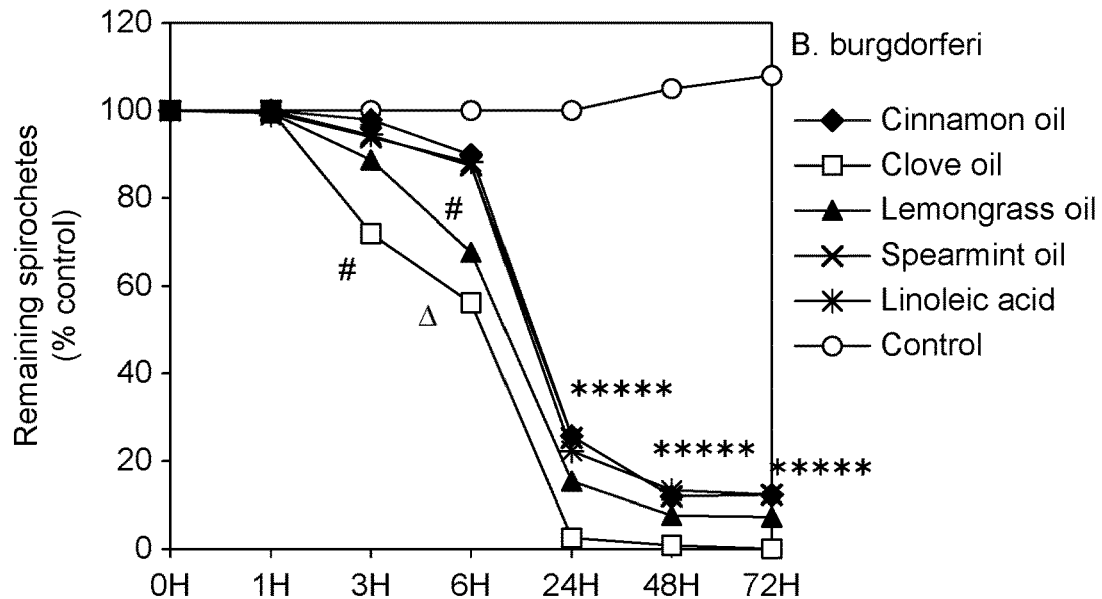
FIGS. 1A, 1B, 1C and 1D: Time-dependent evaluation of the anti-borreliae effect of tested individual compounds used at 0.3 mg/ml concentrations against active (spirochete) form of *Borrelia burgdorferi* and *Borrelia garinii* determined by SYTO9/IP assay staining.
Figure 1B:
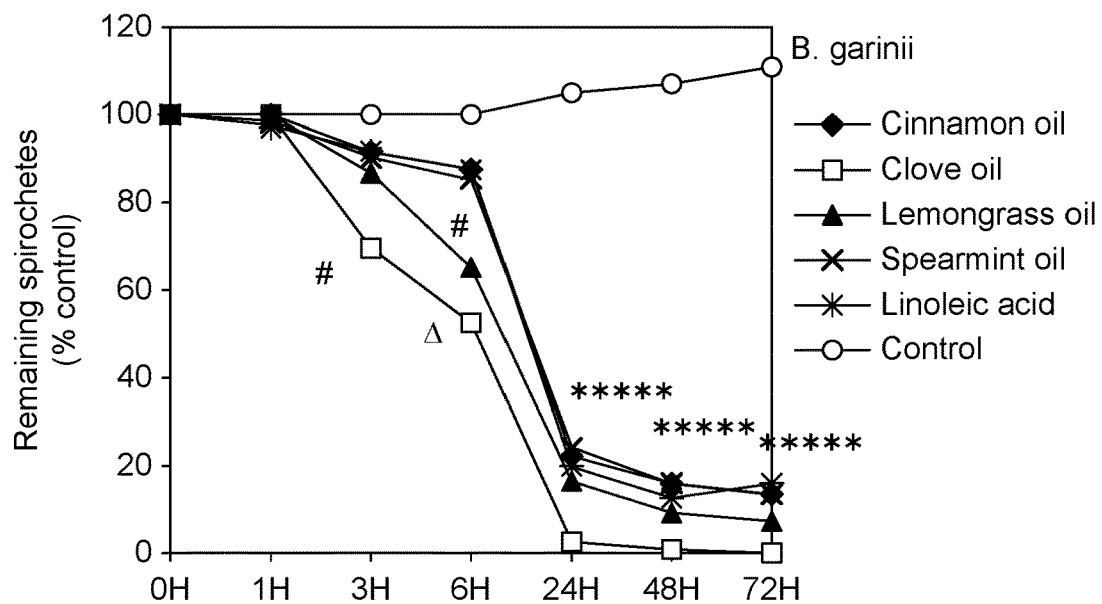
Figure 1C:
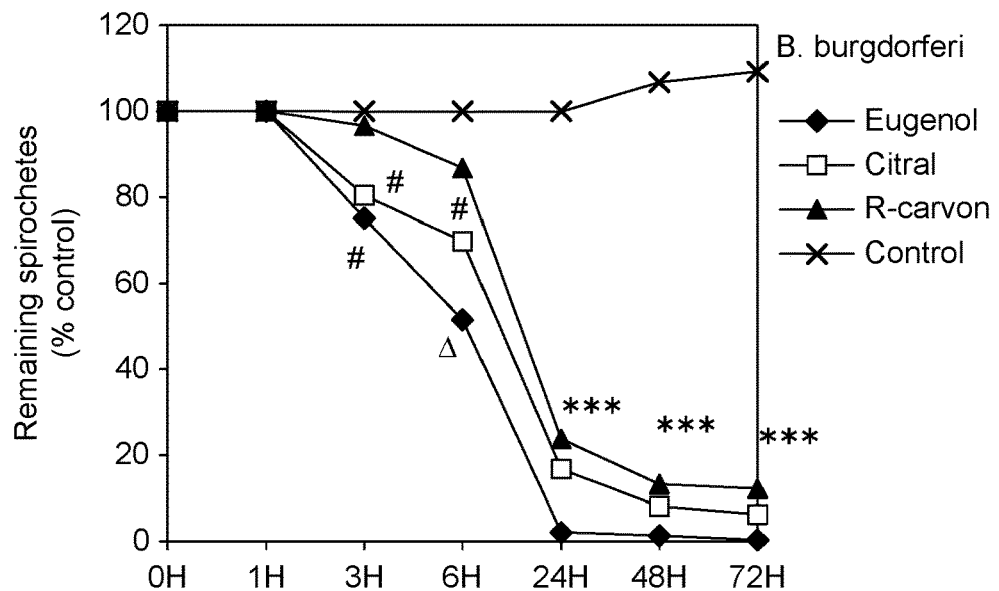
Figure 1D:
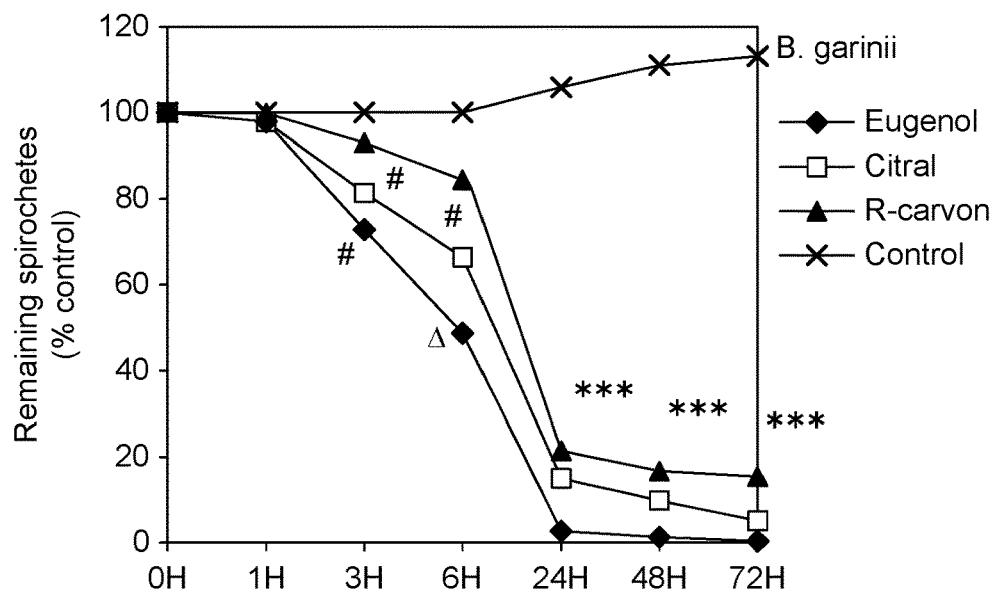
Figure 2A:
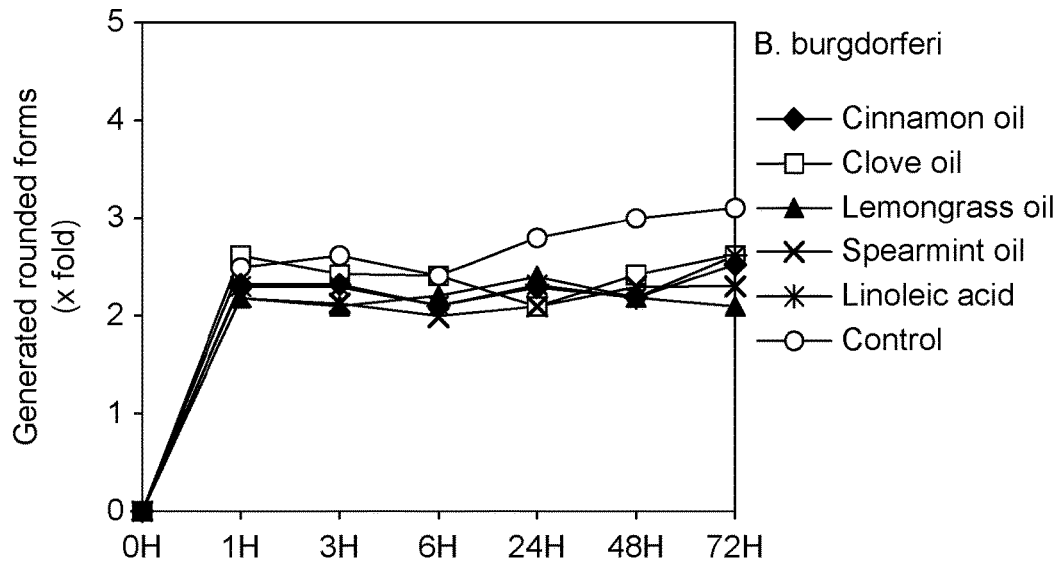
FIGS. 2A, 2B, 2C and 2D: Time-dependent evaluation of the effect of tested individual compounds used at 0.3 mg/ml concentrations against persistent (knob-shaped/rounded) form of *Borrelia burgdorferi* and *Borrelia garinii* determined by SYTO9/IP assay staining.
Figure 2B:
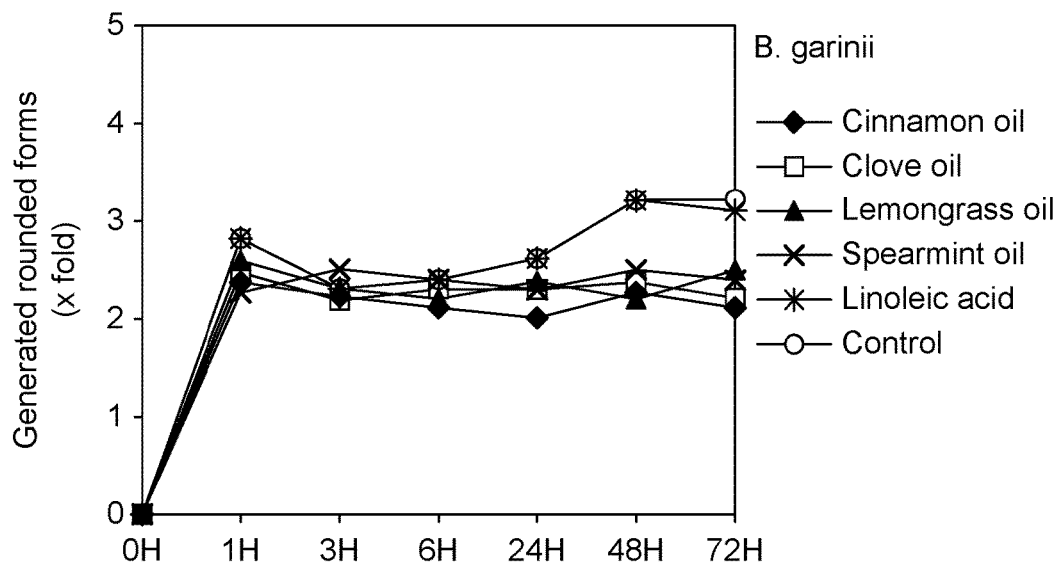
Figure 2C:
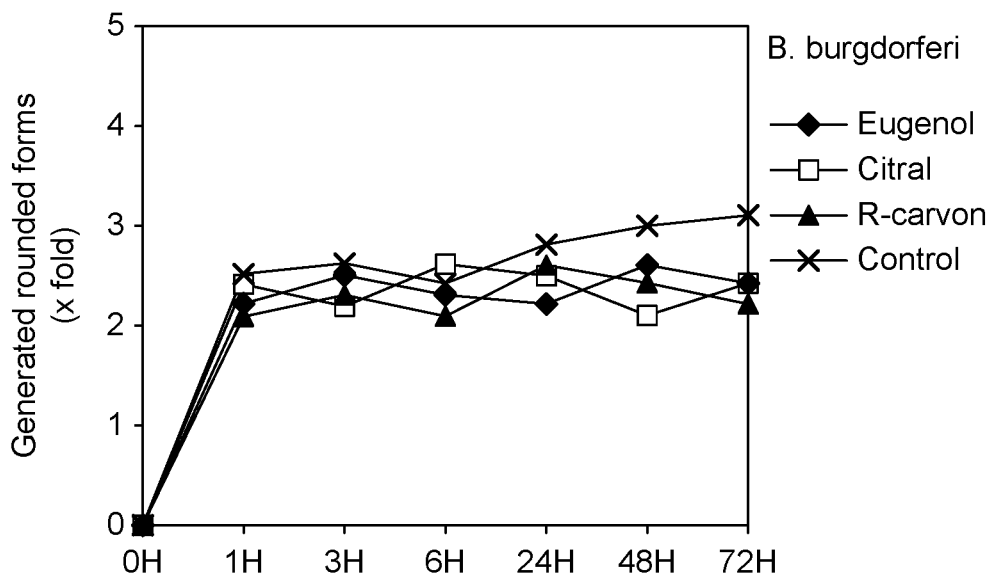
Figure 2D:
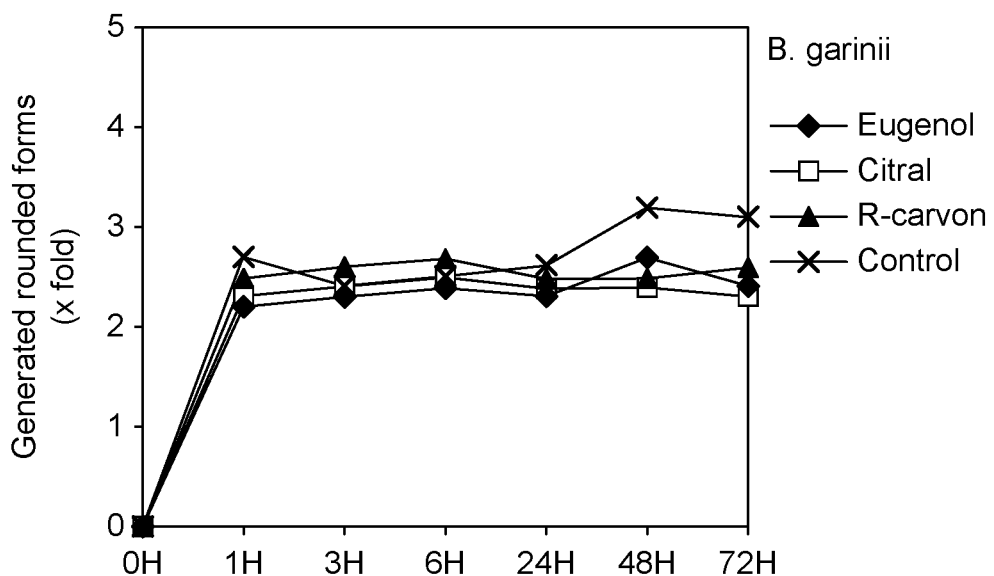
Figure 3A:
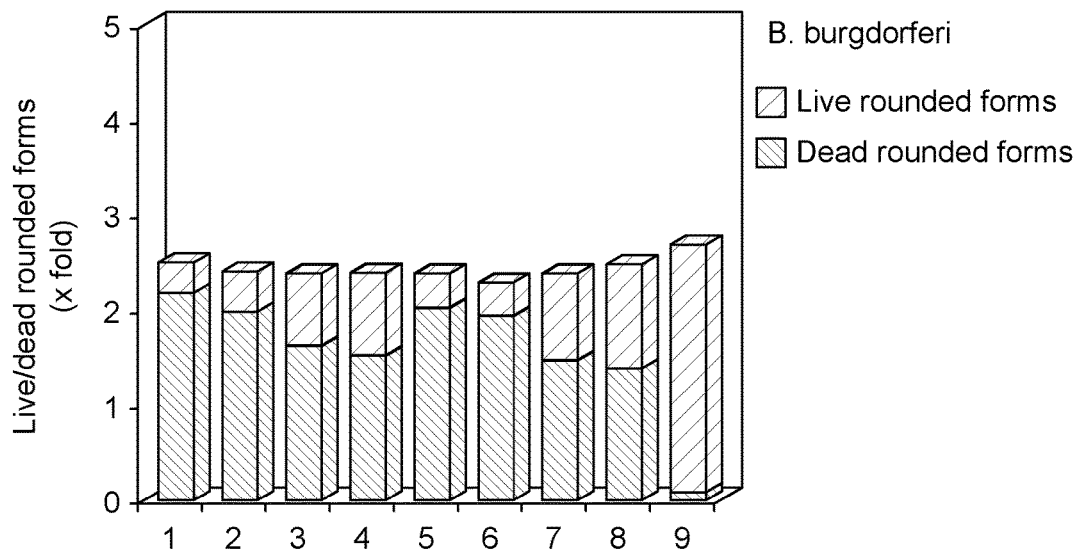
FIGS. 3A and 3B: Live/Dead ratio of rounded forms evaluated after 72 hours post-treatment with tested individual compounds used at 0.3 mg/ml concentrations against persistent (knob-shaped/rounded) form of *Borrelia burgdorferi* and *Borrelia garinii* determined by SYTO9/IP assay staining.
Figure 3B:
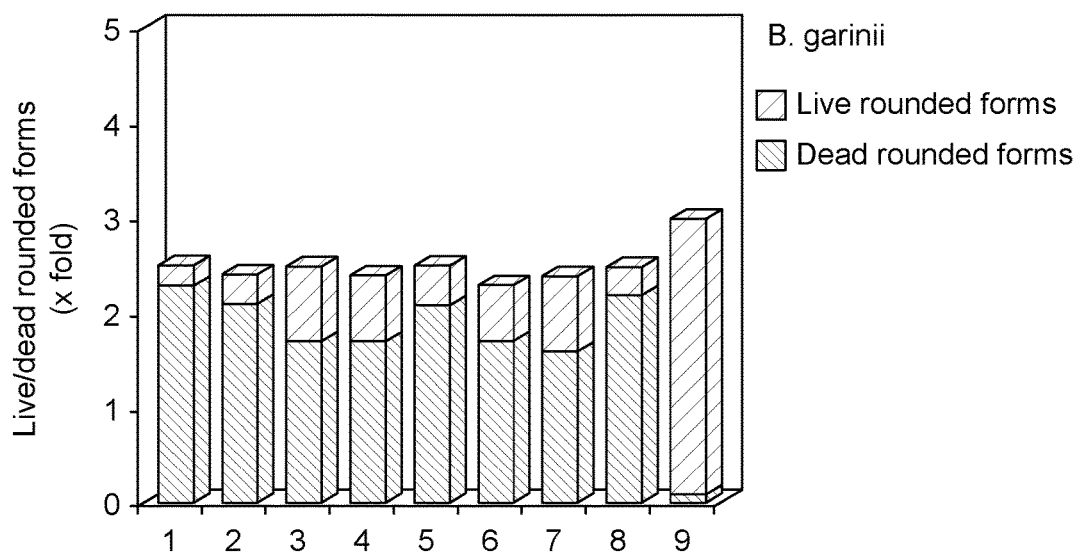

Other features of the present embodiments will be apparent from the accompanying drawings and from the detailed description that follows.

DETAILED DESCRIPTION

Several compositions in various combinations and concentration to test the treatment for Lyme disease using these compositions and simultaneously addressing the treatment of persistent/latent forms, i.e., knob/rounded-shaped form and biofilm and active and motile spirochetes for both the bacteria, i.e., *Borrelia burgdorferi* and *Borrelia garinii* are disclosed. Although the present embodiments have been described with reference to specific example embodiments, it will be evident that various modifications and changes may be made to these embodiments without departing from the broader spirit and scope of the various embodiments. The inventors have designed and prepared novel compositions for use against *Borrelia* sp. infection and in the treatment and/or prevention of Lyme disease. The novel compositions comprise of plant oil extracts and other active chemical compounds applied in different combinations. The novel compositions are effective against both the active (spirochetes) and latent forms (knob/rounded-shaped bodies, biofilm) of *Borrelia* sp.

In embodiments of the invention the experimental results of two compositions comprising plant extracts, essential oils, fatty acids, terpenoids and phenols were tested against active (spirochete) and latent persistent forms (knob/rounded-shaped forms, biofilm) of *Borrelia burgdorferi* and *Borrelia garinii*. The terpenoids are carvone, citral, menthol, camphor, salvinorin etc. Plant extracts like cumin, pomegranate, clove oil, cinnamon oil, thyme and ginger etc., can be used. Examples of essential oils are spearmint oil, lemongrass oil, clove oil, citral, cinnamon oil etc. Fatty acids such as linoleic acid are used for the mixers. The phenols are eugenol etc. The compounds were combined in various mixtures. Mixes 1-8 were prepared are as follows, and Table 1 below further outlines the concentration of the various components in the composition:

Mix 1: linoleic acid, clove oil, lemongrass oil, and spearmint oil or cinnamon oil.

Mix 2: linoleic acid, eugenol, citral and R-carvone or cinnamon oil.

Mix 3: linoleic acid, clove oil and lemongrass oil.

Mix 4: linoleic acid, eugenol and citral.

Mix 5: spearmint oil and/or cinnamon oil, clove oil and lemongrass oil.

Mix 6: R-carvone and/or cinnamon oil, eugenol and citral.

Mix 7: linoleic acid, clove oil and spearmint oil or cinnamon oil.

Mix 8: linoleic acid, eugenol and R-carvone or cinnamon oil

TABLE 1

Compositions of tested mixes against active (spirochete) and persistent forms (knob/rounded-shaped forms, biofilm) of *Borrelia burgdorferi* and *Borrelia garinii*.

| Mix 1 | Mix 2 | Mix 3 | Mix 4 | Mix 5 | Mix 6 | Mix 7 | Mix 8 |
|---|---|---|---|---|---|---|---|
| 0.075 mg/ml Linoleic acid | 0.075 mg/ml Linoleic acid | 0.1 mg/ml Linoleic acid | 0.1 mg/ml Linoleic acid | 0.1 mg/ml Spearmint Oil/Cinnamon oil | 0.1 mg/ml R-carvone/Cinnamon oil | 0.1 mg/ml Linoleic acid | 0.1 mg/ml Linoleic acid |
| 0.075 mg/ml Clove Oil | 0.075 mg/ml Eugenol | 0.1 mg/ml Clove Oil | 0.1 mg/ml Eugenol | 0.1 mg/ml Clove Oil | 0.1 mg/ml Eugenol | 0.1 mg/ml Clove Oil | 0.1 mg/ml Eugenol |
| 0.075 mg/ml Lemongrass Oil | 0.075 mg/ml Citral | 0.1 mg/ml Lemongrass Oil | 0.1 mg/ml Citral | 0.1 mg/ml Lemongrass Oil | 0.1 mg/ml Citral | 0.1 mg/ml Spearmint Oil/Cinnamon oil | 0.1 mg/ml R-carvone/Cinnamon oil |
| 0.075 mg/ml Spearmint Oil/Cinnamon oil | 0.075 mg/ml R-Carvone/Cinnamon oil | | | | | | |

Materials and Methods

Test Compounds.

The following compounds, with the purity between 90%-98% according to the manufacturer, were obtained from Sigma (St. Louis, Mo.): clove oil, eugenol, lemongrass, citral, spearmint oil, cinnamon oil, R-carvone, linoleic acid. As a positive control antibiotic doxycycline (100 mg/mL stock suspension in absolute ethanol) was used, since it is considered a standard therapeutic treatment for patients with Lyme disease.

Test Microorganisms.

Two *Borrelia* species, namely, *Borrelia burgdorferi* and *Borrelia garinii* were tested in this study. Low passage isolates of the B31 strain of *B. burgdorferi* and CIP103362 strain of *B. garinii* were obtained from the American Type Culture Collection (Manassas, Va.). The stocks of both species were cultured in commonly used conditions, i.e. medium such as Barbour-Stoner-Kelly H (BSK-H) supplemented with 6% rabbit serum (Sigma, St Louis, Mo.) without antibiotics at 33° C. with 5% $CO_2$, in sterile screw-cap 15 mL polypropylene tubes with or without gentile shaking depends on type of experiment. B31 strain is an isolate from *Ixodes dammini* whereas CIP103362 strain is an isolate from *Ixodes ricinus*. Both strains are well known human pathogenic factors of Lyme disease. So far, *Borrelia burgdorferi* has been found in ticks from North America and Eurasia, while *Borrelia garinii* only in ticks in Eurasia.

Preparation of Test Microorganisms for Susceptibility Testing.

The strains of *B. burgdorferi* and *B. garinii* were prepared for testing as described in the art (Sapi et al., 2011). Briefly, the strains were activated from original cryobank vials and inoculated into 10 mL BSK-H compete medium, and maintained at 33° C. For generation of homogeneous cultures of *B. burgdorferi* or *B. garinii*, bacterial cells were inoculated and maintained in a shaking incubator at 33° C. and 250 rpm, where there is no biofilm formation (Sapi et al., 2011; supported by own observation). For generation of biofilm-like colonies of *B. burgdorferi* or *B. garinii*, bacterial cells were inoculated in four-well chambers (BD Biosciences, Sparks, Md.) coated with rat-tail collagen type I and incubated for 1 week without shaking.

Figure 4:
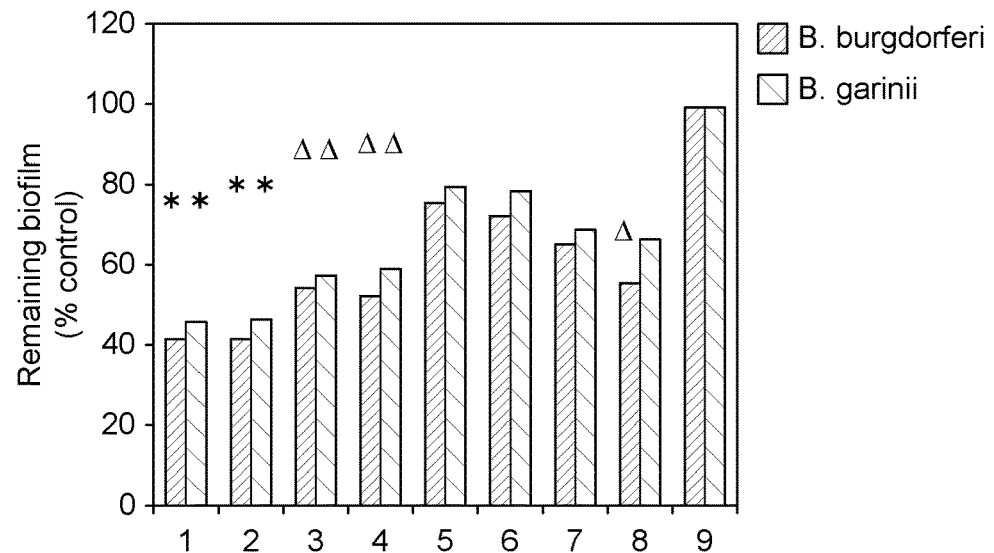
FIG. 4: Evaluation of the anti-borreliae effect of tested individual compounds used at 0.3 mg/ml concentrations against persistent (biofilm) form of *Borrelia burgdorferi* and *Borrelia garinii* determined by SYTO9/IP assay staining.
Figure 5A:
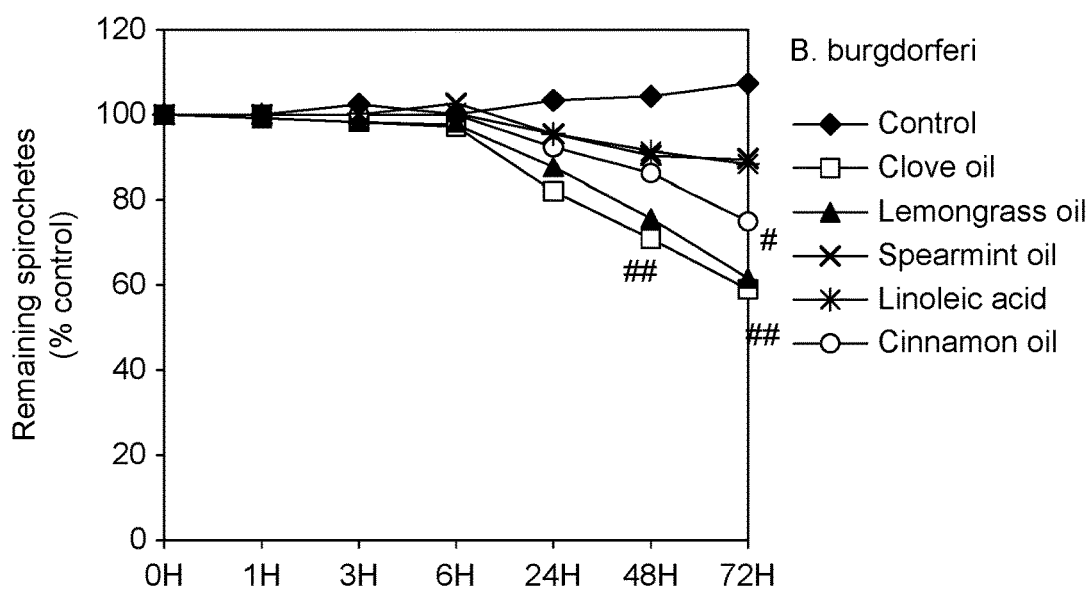
FIGS. 5A, 5B, 5C and 5D: Time-dependent evaluation of the anti-borreliae effect of tested individual compounds used at 0.075 mg/ml concentrations against active (spirochete) form of *Borrelia burgdorferi* and *Borrelia garinii* determined by SYTO9/IP assay staining.
Figure 5B:
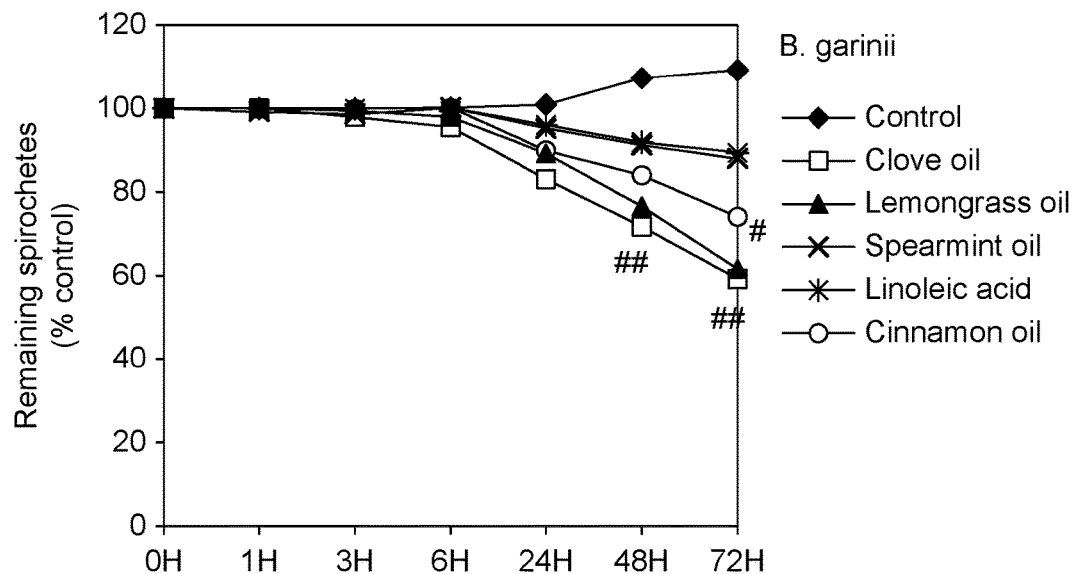
Figure 5C:
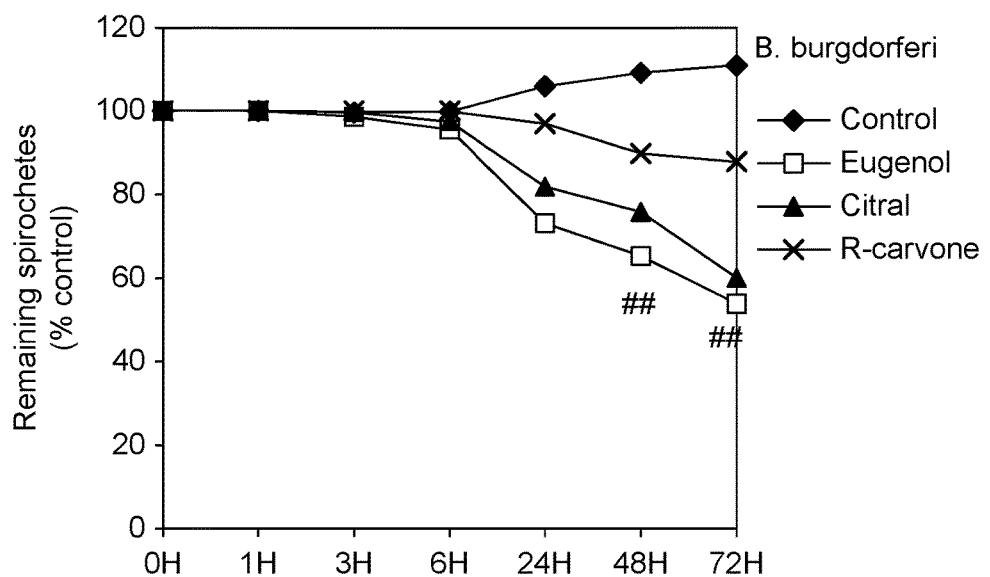
Figure 5D:
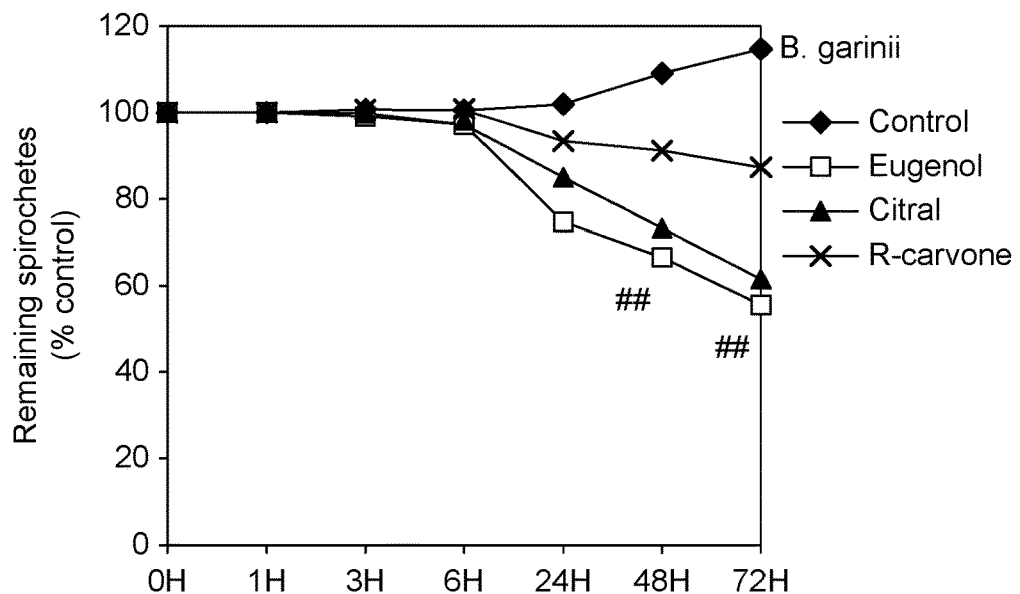
Figure 6A:
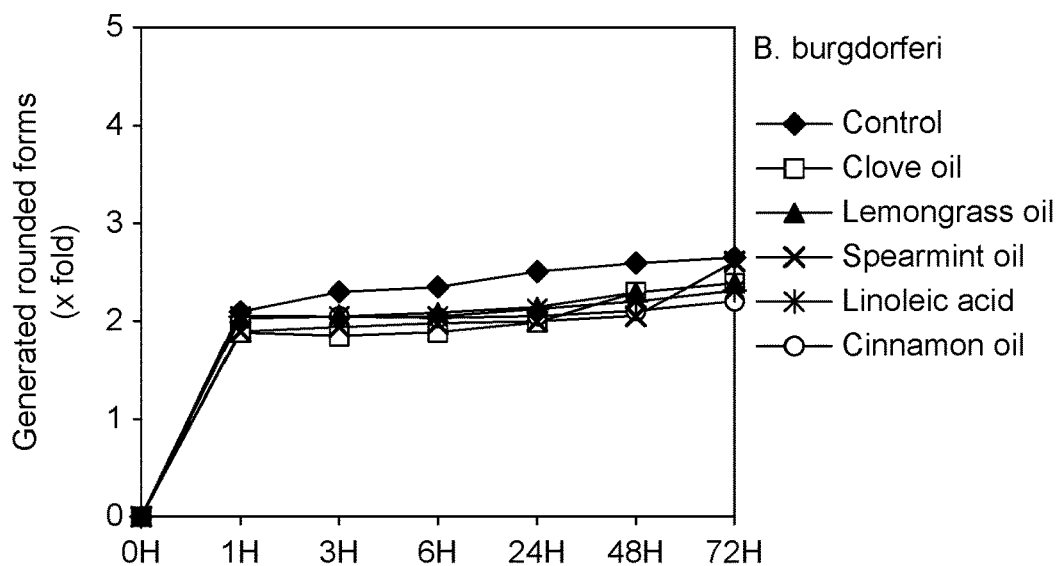
FIGS. 6A, 6B, 6C and 6D: Time-dependent evaluation of the effect of tested individual compounds used at 0.075 mg/ml concentrations against persistent (knob-shaped/rounded) form of *Borrelia burgdorferi* and *Borrelia garinii* determined by SYTO9/IP assay staining.
Figure 6B:
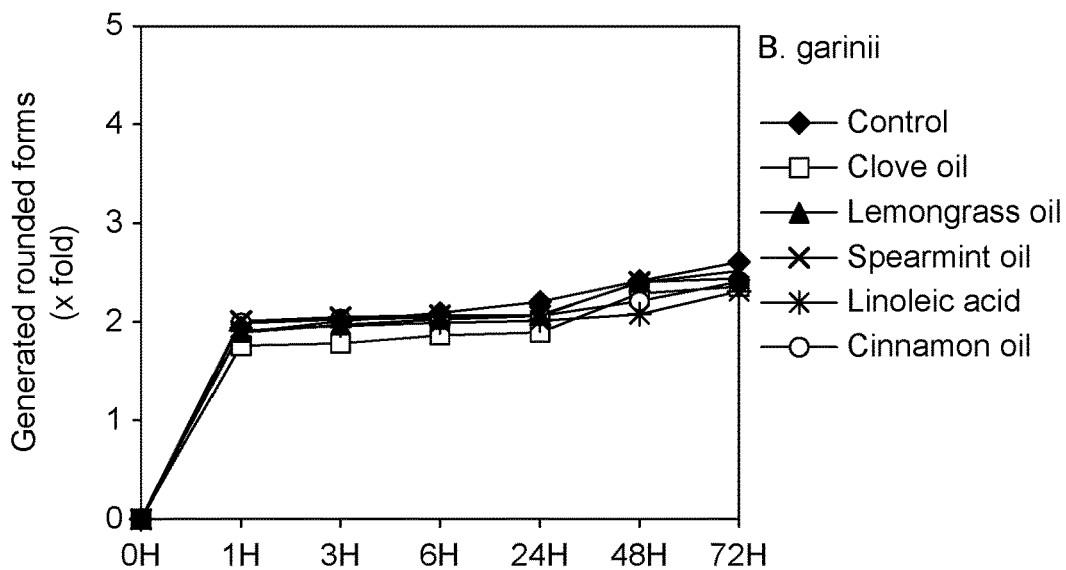
Figure 6C:
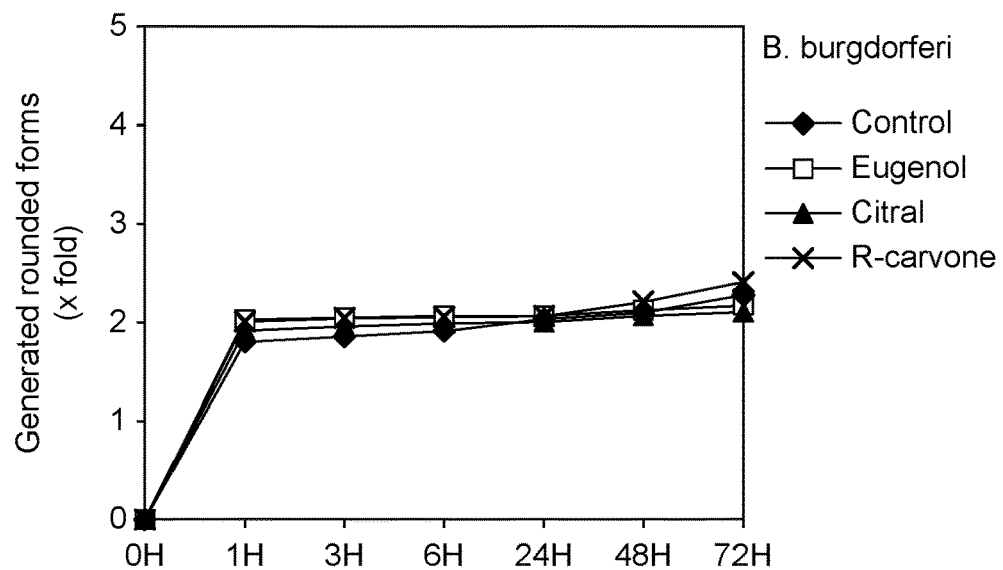
Figure 6D:
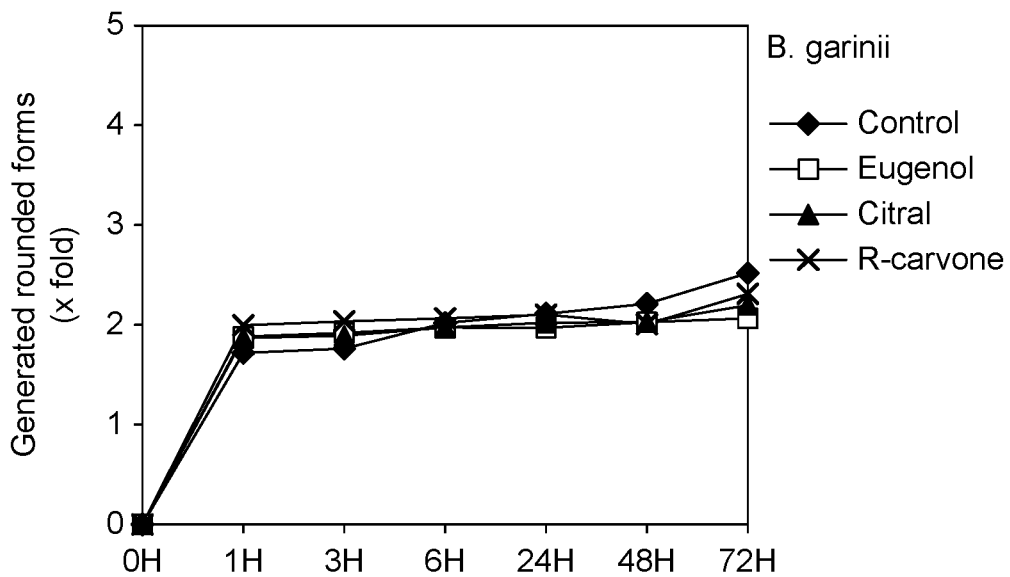

Evaluation of bacteriostatic and bactericidal effect of individual test compounds and their mixtures on test microorganisms. To determine what compound and/or mixture will have the bacteriostatic and/or bactericidal effect a fluorescence method was used according to Sapi et al. Briefly, $5 \times 10^6$ bacterial cells/mL of the homogenous bacterial suspension was inoculated into each sterile 1.8 mL test tightly caps screwed tubes containing 1 mL BSK-H medium, supplemented with the test compound/mixture of interest. Control cultures were treated with ethanol (i.e., 0.075-0.3 mg/ml) alone. For doxycycline, as a positive control, the final used concentration was 0.075-0.3 mg/ml). The tubes were then incubated at 33° C. and viability was monitored at regular intervals for up to 72 hours. The whole experiment was repeated three times for each strain and each concentration. The susceptibility of spirochetes and knob/rounded-shaped body forms to the test compound was then assessed after 1 hour, 3 hours, 6 hours, 24 hours, 48 hours, 72 hours by LIVE/DEAD® BacLight™ Bacterial Viability Assay using fluorescent microscopy, were the ratio of live (green) and dead (red) *B. burgdorferi* and *B. garinii* morphological forms were calculated. The composition is administered to mammals to treat Lyme disease. The mode of administration includes, but not limited to, non-invasive perioral, topical (example transdermal), enteral, transmucosal, targeted delivery, sustained release delivery, delayed release, pulsed release and parenteral methods. Various combinations of these administration modes may be combined.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of the composition as active ingredient.

Evaluation of test compounds/mixtures on bacterial biofilm. Qualitative effect of the individual test compounds and their mixtures against biofilm-like colonies of *B. burgdorferi* and *B. garinii* was evaluated using commonly used and well accepted crystal violet (CV) staining method, according to protocol provided by Sapi et al. Briefly, $1\times10^7$ bacterial cells/mL from homogeneous cultures of spirochetes were grown on extracellular matrix proteins (i.e., collagen type I) coated four-well chambers and incubated for 1 week.

After the 1 week of incubation, biofilm-like colonies were treated with various compounds/mixtures. Control wells were treated with ethanol (i.e., 0.075-0.3 mg/ml) alone. For doxycycline, as a positive control, the final used concentration was 0.03% (v/v). The chambers were then incubated at 33° C. for 72 hours. The whole experiment was repeated three times for each strain and each concentration. Next, all wells were fixed with 500 μL of cold methanol-formalin (1:1) for 30 minutes and stained with 1 mL of crystal violet (0.1%) for 10 minutes. The biofilm-like colonies were carefully washed three times with 1×PBS and 1 mL of methanol was added to each well to extract a dye, which was measured at 595 nm wavelength.

Statistical Analysis.

Means and standard deviations were determined for all experiments and Student's t test analysis was used to determine significant differences. Statistical analysis was performed by t-test using GraphPad statistical software. COLBY equation was applied to calculate synergistic cooperation of the components in the test mixtures as described (Ferry N, Stanley B H, Armel G. 2005, Design and analysis of biological assay of mixtures. $17^{th}$ Annual Conference on Applied Statistics in Agriculture, Kansas State University Libraries, New Prairie Press).

FIGS. 1A, 1B, 1C and 1D: Time-dependent evaluation of the anti-borreliae effect of tested individual compounds against active (spirochete) form of *Borrelia burgdorferi* and *Borrelia garinii* determined by SYTO9/IP assay staining. Tested ingredients: clove oil (0.3 mg/ml), lemongrass oil (0.3 mg/ml), spearmint oil (0.3 mg/ml), linoleic acid (0.3 mg/ml), eugenol (0.3 mg/ml), citral (0.3 mg/ml), R-carvone (0.3 mg/ml), cinnamon oil (0.3 mg/ml), control (0.3 mg/ml ethanol); # $p\leq0.05$, $\Delta p\leq0.01$, $*p\leq0.001$. The results show 50% bactericidal effect against *B. burgdorferi* and *B. garinii* was achieved by clove oil and its main active constituent eugenol after 6 hours of incubation. 100% bactericidal effect was achieved after 24 hours of incubation with these agents. The rest of tested compounds revealed 75-90% bactericidal effect after 24-72 hours of incubation.

FIGS. 2A, 2B, 2C and 2D: Time-dependent evaluation of the anti-borreliae effect of tested individual compounds against persistent (rounded) form of *Borrelia burgdorferi* and *Borrelia garinii* determined by SYTO9/IP assay staining. Tested ingredients: clove oil (0.3 mg/ml), lemongrass oil (0.3 mg/ml), spearmint oil (0.3 mg/ml), linoleic acid (0.3 mg/ml), eugenol (0.3 mg/ml), citral (0.3 mg/ml), R-carvone (0.3 mg/ml), cinnamon oil (0.3 mg/ml), control (0.3 mg/ml ethanol). All tested agents did not stimulate generation of latent rounded forms of *B. burgdorferi* and *B. garinii* from spirochetes compared to controls.

FIGS. 3A and 3B: Live/Dead ratio of rounded forms evaluated after 72 hours post-treatment with tested individual compounds against persistent (rounded) form of *Borrelia burgdorferi* and *Borrelia garinii* determined by SYTO9/IP assay staining. Tested ingredients: 1—clove oil (0.3 mg/ml), 2—eugenol (0.3 mg/ml), 3—lemongrass oil (0.3 mg/ml), 4—citral (0.3 mg/ml), 5—spearmint oil (0.3 mg/ml), 6—R-carvone (0.3 mg/ml); 7—linoleic acid (0.3 mg/ml), 8—cinnamon oil (0.3 mg/ml), 9—control (0.3 mg/ml ethanol). Latent rounded forms of *B. burgdorferi* and *B. garinii* are susceptible to the treatment with all tested agents, at these concentrations.

FIG. 4: Evaluation of the anti-borreliae effect of tested individual compounds against persistent (biofilm) form of Borrelia burgdorferi and Borrelia garinii determined by SYTO9/IP assay staining. Tested ingredients: 1—clove oil (0.3 mg/ml), 2—eugenol (0.3 mg/ml), 3—lemongrass oil (0.3 mg/ml), 4—citral (0.3 mg/ml), 5—spearmint oil (0.3 mg/ml), 6—R-carvone (0.3 mg/ml); 7—linoleic acid (0.3 mg/ml), 8—cinnamon oil (0.3 mg/ml), 9—control (0.03 mg/ml ethanol); $\Delta p \leq 0.01$, *$p \leq 0.001$. Biofilms of B. burgdorferi and B. garinii are susceptible to the treatment with clove oil and its main active constituent eugenol as well as lemongrass and its main active constituent citral at used concentrations.

FIGS. 5A and 5B, 5C and 5D: Time-dependent evaluation of the anti-borreliae effect of tested individual compounds used at 0.075 mg/ml concentrations against active (spirochete) form of Borrelia burgdorferi and Borrelia garinii determined by SYTO9/IP assay staining.

Figure 7A:
FIGS. 7A and 7B: Live/Dead ratio of rounded forms evaluated after 72 hours post-treatment with tested individual compounds used at 0.075 mg/ml concentrations against persistent (knob-shaped/rounded) form of *Borrelia burgdorferi* and *Borrelia garinii* determined by SYTO9/IP assay staining.
Figure 7B:
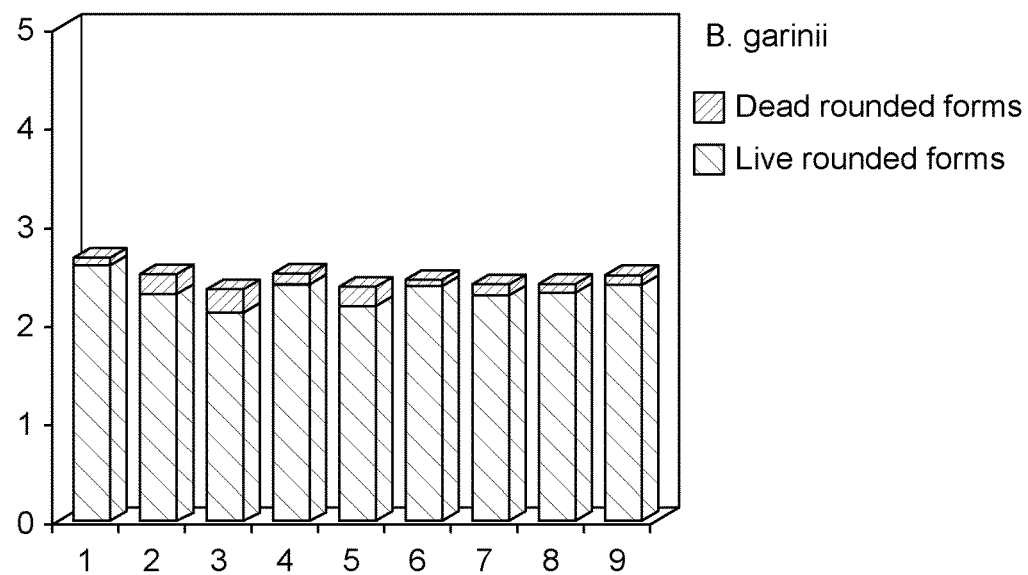

FIGS. 6A, 6B, 6C and 6D; Time-dependent evaluation of the anti-borreliae effect of tested individual compounds used at 0.075 mg/ml concentrations against persistent (knob-shaped/rounded) forms of Borrelia burgdorferi and Borrelia garinii determined by SYTO9/IP assay staining FIGS. 7A and 7B: Live/Dead ratio of rounded forms evaluated after 72 hours post-treatment with tested individual compounds used at 0.075 mg/ml concentrations against persistent (knob-shaped/rounded) form of Borrelia burgdorferi and Borrelia garinii determined by SYTO9/IP assay staining.

Figure 8:
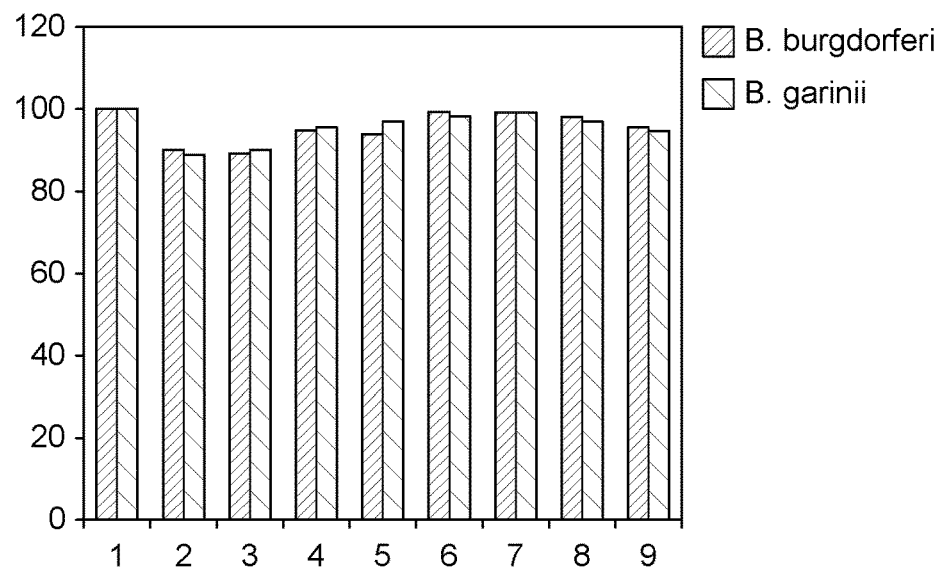
FIG. 8: Evaluation of the anti-borreliae effect of tested individual compounds used at 0.075 mg/ml concentrations against persistent (biofilm) form of *Borrelia burgdorferi* and *Borrelia garinii* determined by SYTO9/IP assay staining.
Figure 9A:
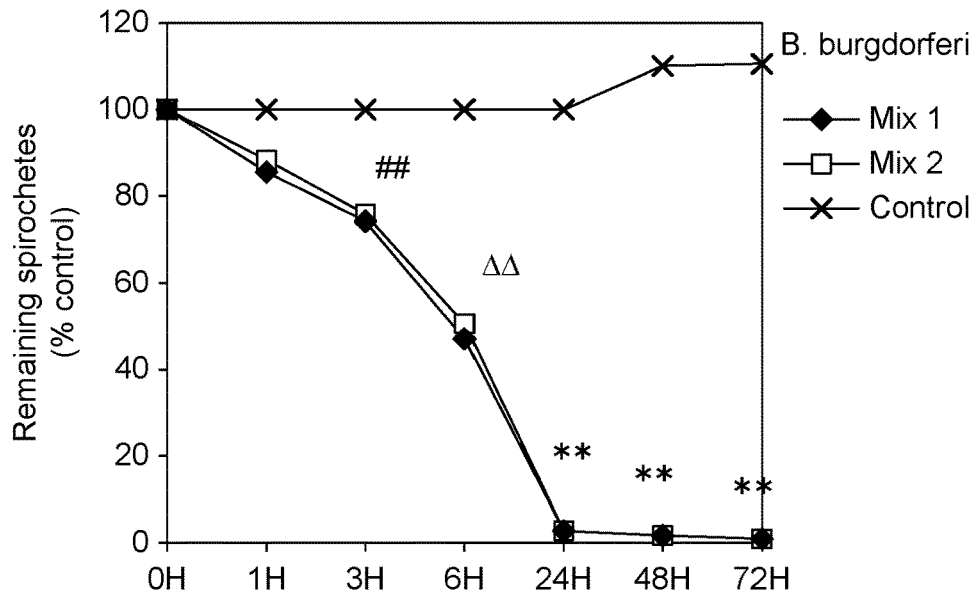
FIGS. 9A and 9B: Time-dependent evaluation of the anti-borreliae effect of tested mixes against active (spirochete) form of *Borrelia burgdorferi* and *Borrelia garinii* determined by SYTO9/IP assay staining.
Figure 9B:
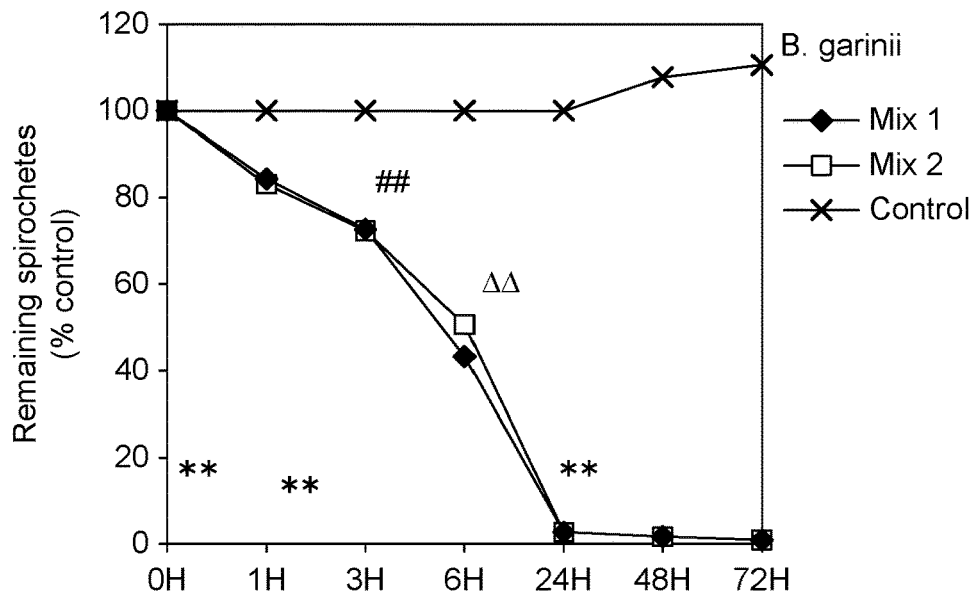

FIG. 8: Evaluation of the anti-borreliae effect of tested individual compounds used at 0.075 mg/ml concentrations against persistent (biofilm) form of Borrelia burgdorferi and Borrelia garinii determined by SYTO9/IP assay FIGS. 9A and 9B: Time dependent evaluation of the anti-boreliae effects of tested mixes (Mix 1 and Mix 2) against active (spirochete) form of Borrelia burgdorferi and Borrelia garinii determined by SYTO9/IP assay staining. Tested mixes contained: Mix 1: clove oil (0.075 mg/ml), lemongrass oil (0.075 mg/ml), spearmint oil (0.075 mg/ml) or cinnamon oil (0.075 mg/ml), linoleic acid (0.075 mg/ml); Mix 2: eugenol (0.075 mg/ml), citral (0.075 mg/ml), linoleic acid (0.075 mg/ml, R-carvone (0.075 mg/ml) or cinnamon oil (0.075 mg/ml). Control (0.3 mg/ml ethanol). # $p \leq 0.05$, $\Delta p \leq 0.01$, *$p \leq 0.001$. The results shows that c.a. 50% bactericidal effect against B. burgdorferi and B. garinii was achieved by all tested mixtures (composition provided in Table 1) after 6 hours of incubation. 100% bactericidal effect was achieved after 24 hours of incubation with these mixtures.

Figure 10A:
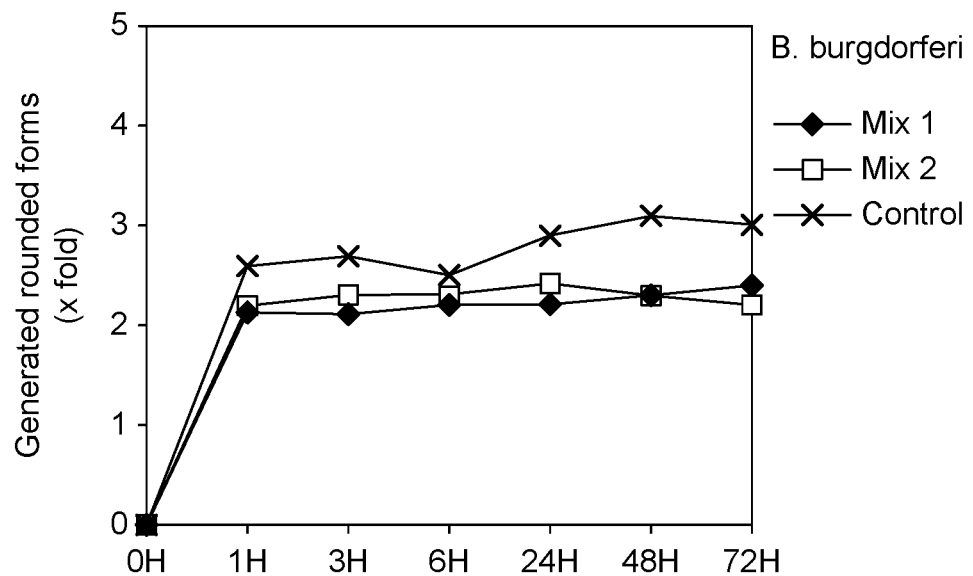
FIGS. 10A and 10B: Time-dependent evaluation of the anti-borreliae effect of tested mixes against persistent (rounded) form of *Borrelia burgdorferi* and *Borrelia garinii* determined by SYTO9/IP assay staining.
Figure 10B:
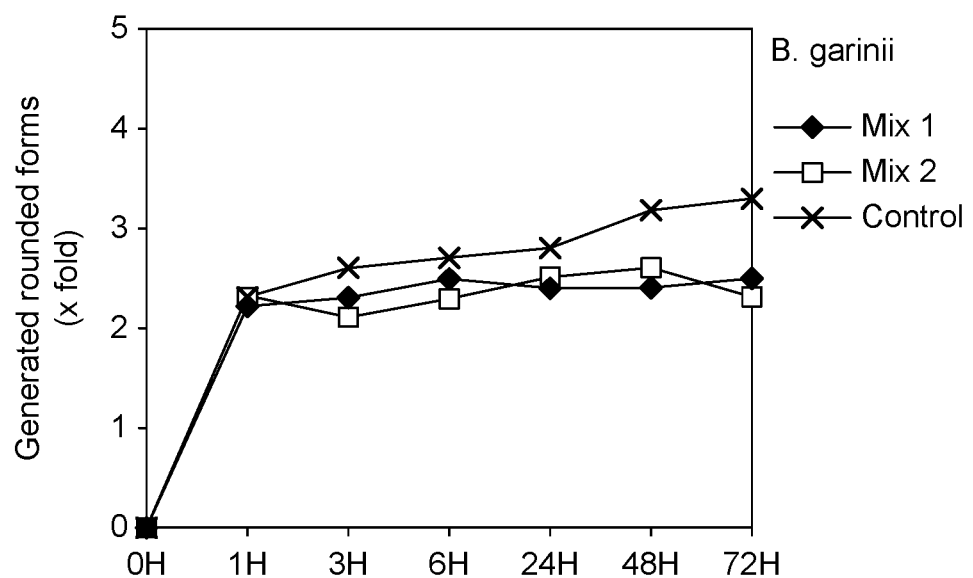

FIGS. 10A and 10B: Time-dependent evaluation of the anti-borreliae effect of tested mixes against persistent (knob-shaped/rounded) form of Borrelia burgdorferi and Borrelia garinii determined by SYTO9/IP assay staining. Tested mixes contained: Mix 1: clove oil (0.075 mg/ml), lemongrass oil (0.075 mg/ml), spearmint oil (0.075 mg/ml) or cinnamon oil (0.075 mg/ml), linoleic acid (0.075 mg/ml); Mix 2: eugenol (0.075 mg/ml), citral (0.075 mg/ml), linoleic acid (0.075 mg/ml), R-carvone (0.075 mg/ml) or cinnamon oil (0.075 mg/ml); Control (0.075 mg/ml ethanol). All tested mixtures do not generate latent knob/rounded-shaped forms of B. burgdorferi and B. garinii.

Figure 11:
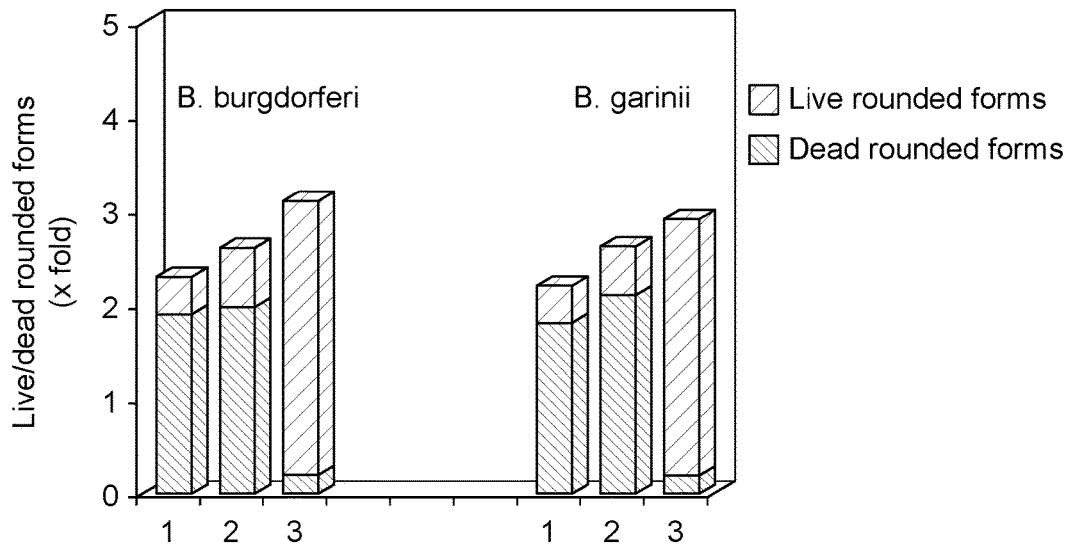
FIG. 11: Live/Dead ratio of rounded forms evaluated after 72 hours post-treatment with tested mixes (1-2) against persistent (knob-shaped/rounded) form of *Borrelia burgdorferi* and *Borrelia garinii* determined by SYTO9/IP assay staining.

FIG. 11: Live/Dead ratio of rounded forms evaluated after 72 hours post-treatment with tested mixes (1-2) against persistent (rounded) form of Borrelia burgdorferi and Borrelia garinii determined by SYTO9/IP assay staining. Tested mixes contained: Mix 1: clove oil (0.075 mg/ml), lemongrass oil (0.075 mg/ml), spearmint oil (0.075 mg/ml) or cinnamon oil (0.075 mg/ml), linoleic acid (0.075 mg/ml); Mix 2: eugenol (0.075 mg/ml), citral (0.075 mg/ml), linoleic acid (0.075 mg/ml), R-carvone (0.075 mg/ml) or cinnamon oil (0.075 mg/ml); Control (0.075 mg/ml ethanol. Latent rounded forms of B. burgdorferi and B. garinii are susceptible to the treatment with tested mixtures (more than 2-fold increase in dead latent forms compared to control that contains mostly alive forms).

Figure 12:
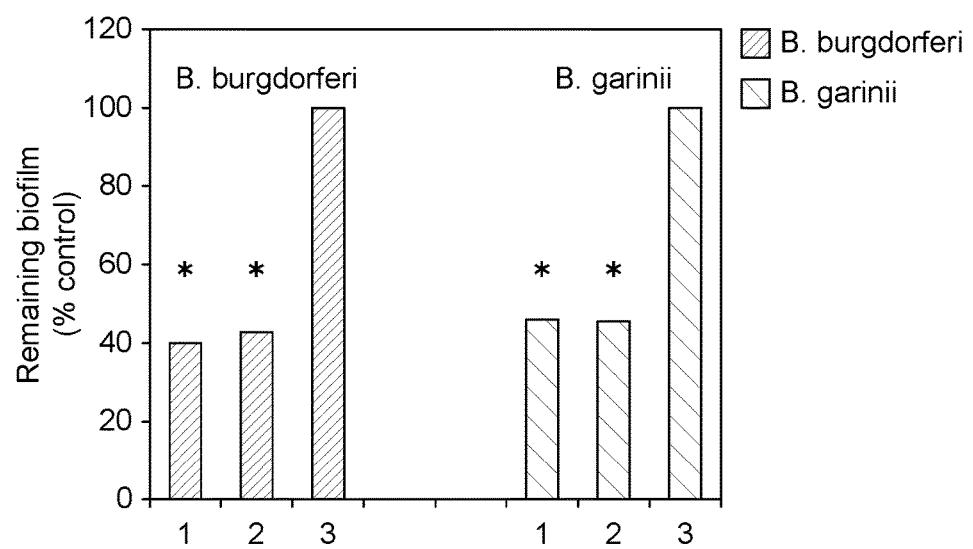
FIG. 12: Evaluation of the anti-borreliae effect of tested mixes against persistent (biofilm) form of *Borrelia burgdorferi* and *Borrelia garinii* determined by SYTO9/IP assay staining.
Figure 13A:
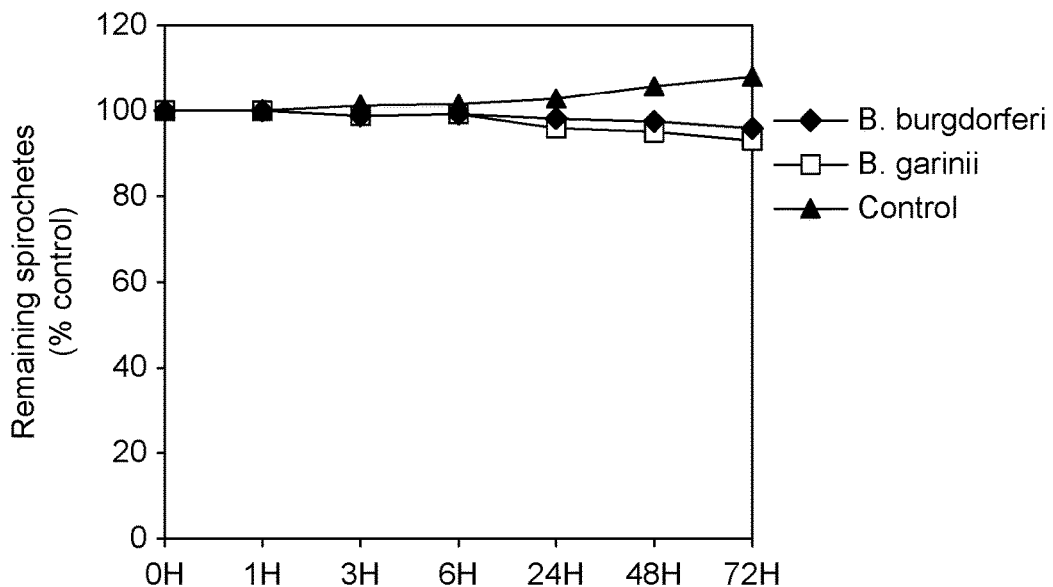
Figure 13B:
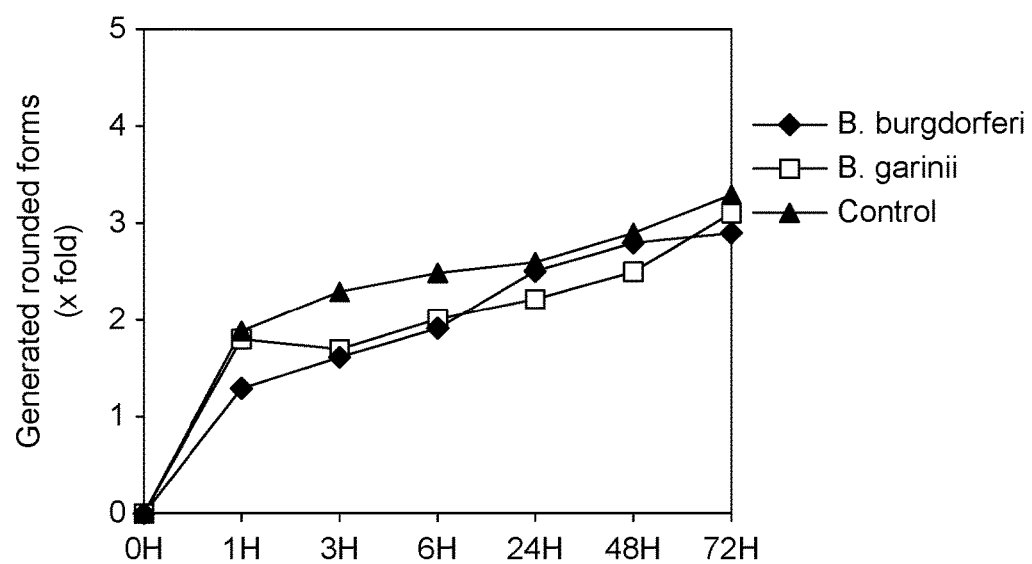

FIG. 12 Evaluation of the anti-borreliae effect of tested mixes against persistent (biofilm) form of Borrelia burgdorferi and Borrelia garinii determined by SYTO9/IP assay staining. Tested mixes contained: Mix 1: clove oil (0.075 mg/ml), lemongrass oil (0.075 mg/ml), spearmint oil (0.075 mg/ml) or cinnamon oil (0.075 mg/ml), linoleic acid (0.075 mg/ml); Mix 2: eugenol (0.075 mg/ml), citral (0.075 mg/ml), linoleic acid (0.075 mg/ml), R-carvone (0.075 mg/ml) or cinnamon oil (0.075 mg/ml); Control (0.075 mg/ml ethanol *$p \leq 0.001$. Biofilms of B. burgdorferi and B. garinii are susceptible to the treatment with both tested mixtures (biofilm eliminated in about 60%).

FIGS. 13A, 13B, 13C and 13D: Evaluation of the anti-borreliae effect of doxycycline against active (spirochete) and persistent forms (rounded forms, biofilm) of Borrelia burgdorferi and Borrelia garinii determined by SYTO9/IP staining; doxycycline (0.3 mg/ml), control (0.3 mg/ml ethanol). Neither spirochetes nor latent forms (knob-shaped/rounded forms, biofilm) of B. burgdorferi and B. garinii are susceptible to doxycycline treatment used at the same concentration as tested compounds and mixtures.

TABLE 2: Colby calculations (Colby, 1967) were conducted in order to determine whether the effect of the ingredients combined in form of different mixes was based on their synergistic, additive or antagonistic interactions. Data obtained from the calculation are outlined in Table 2 below. The results show that synergistic effects were obtained in all cases. No antagonistic effect was obtained. Instant results as shown in figures prove that for individual ingredients that were tested at two tested concentrations: 0,075 mg/ml and 0.3 mg/ml in order to show that individual ingredients at low concentrations are not very effective, but they become effective as a mixture. Using these nutrient combinations one may avoid any possible toxicity of high doses of individual components, enhance their absorption and utilization and maintain metabolism in balance. These results further prove synergistic effect applicable as a treatment for Lyme disease and all forms of the bacteria simultaneously using one mixture.

TABLE 2

| | Colby calculation. | | | | | |
|---|---|---|---|---|---|---|
| | B. burgdorferi Spirochetes | | B. garinii Spirochetes | | B. burgdorferi Rounded forms/Persisters | |
| Mix | Observed | Expected | Observed | Expected | Observed | Expected |
| Mix 1 | 99.9 ± 9.8 | 87.5 ± 3.0* | 99.9 ± 10.1 | 89.3 ± 3.4* | 90.9 ± 9.9 | 52.6 ± 5.0# |
| Mix 2 | 99.9 ± 9.6 | 88.9 ± 3.7* | 99.9 ± 10.8 | 89.5 ± 4.3* | 91.2 ± 9.5 | 57.0 ± 6.1# |

TABLE 2-continued

Colby calculation.

| Mix | B. burgdorferi Spirochetes | | B. garinii Spirochetes | | B. burgdorferi Rounded forms/Persisters | |
|---|---|---|---|---|---|---|
| | Observed | Expected | Observed | Expected | Observed | Expected |
| Mix 3 | 99.9 ± 10.1 | 91.8 ± 2.9* | 99.9 ± 11.1 | 92.3 ± 3.7* | 89.8 ± 10.2 | 63.4 ± 5.8# |
| Mix 4 | 99.9 ± 11.2 | 92.8 ± 3.5* | 99.9 ± 10.9 | 93.2 ± 3.5* | 88.9 ± 11.4 | 65.2 ± 5.5# |
| Mix 5 | 99.9 ± 8.6 | 91.1 ± 4.2* | 99.9 ± 9.7 | 91.6 ± 4.0* | 90.4 ± 10.9 | 61.9 ± 6.0# |
| Mix 6 | 99.9 ± 8.9 | 91.6 ± 4.2* | 99.9 ± 8.9 | 92.4 ± 4.0* | 90.2 ± 9.7 | 63.4 ± 6.1# |
| Mix 7 | 99.9 ± 9.7 | 90.2 ± 5.0* | 99.9 ± 10.6 | 92.1 ± 4.0* | 89.7 ± 8.6 | 55.9 ± 7.2# |
| Mix 8 | 99.9 ± 11.2 | 91.5 ± 4.4* | 99.9 ± 9.9 | 91.4 ± 4.3* | 90.7 ± 10.3 | 57.6 ± 6.7# |

TABLE 3

Colby calculation.

| Mix | B. garinii Rounded forms/Persisters | | B. burgdorferi Biofilm | | B. garinii Biofilm | |
|---|---|---|---|---|---|---|
| | Observed | Expected | Observed | Expected | Observed | Expected |
| Mix 1 | 90.4 ± 8.8 | 55.0 ± 6.0# | 60.3 ± 6.8 | 55.7 ± 6.6* | 57.3 ± 4.1 | 53.6 ± 4.8* |
| Mix 2 | 90.5 ± 10.8 | 57.4 ± 6.2# | 60.6 ± 7.2 | 52.3 ± 6.6* | 57.6 ± 5.0 | 52.6 ± 4.8* |
| Mix 3 | 90.2 ± 11.1 | 65.4 ± 6.0# | 61.3 ± 5.9 | 46.9 ± 6.2* | 59.9 ± 5.7 | 48.2 ± 6.1* |
| Mix 4 | 89.5 ± 10.9 | 70.0 ± 5.0# | 59.3 ± 6.2 | 46.0 ± 6.3* | 58.6 ± 5.2 | 47.3 ± 6.2* |
| Mix 5 | 90.1 ± 8.7 | 64.0 ± 5.8# | 60.7 ± 5.3 | 47.5 ± 6.1* | 53.3 ± 4.6 | 48.9 ± 6.1* |
| Mix 6 | 90.5 ± 9.3 | 68.8 ± 5.4# | 60.8 ± 5.4 | 46.2 ± 6.0* | 54.9 ± 6.1 | 46.5 ± 6.3* |
| Mix 7 | 90.0 ± 8.8 | 58.5 ± 6.8# | 59.9 ± 6.3 | 45.0 ± 6.3* | 55.2 ± 5.8 | 48.3 ± 6.1* |
| Mix 8 | 90.3 ± 10.7 | 57.7 ± 6.9# | 58.2 ± 6.8 | 46.0 ± 6.1* | 55.4 ± 5.7 | 47.0 ± 6.3* |

COLBY calculation: according to Ferry et al. (2005), DESIGN AND ANALYSIS OF BIOLOGICAL ASSAYS OF MIXTURES; Annual Conference on Applied Statistics in Agriculture.
Observed > Expected COLBY = synergistic effect, Observed < Expected COLBY = antagonistic effect;
*$p < 0.05$,
$p < 0.01$ As used herein when referring to numerical values or percentages, the term "about" includes variations due to the methods used to determine the values or percentages, statistical variance and human error. Moreover, each numerical parameter in this application should at least be construed in light of the number of reported significant digits and by applying ordinary rounding techniques.

INDUSTRIAL APPLICABILITY

Various compositions according to the invention are useful in the treatment and/or prevention of *Borrelia burgdorferi* and *Borrelia garinii* infection that is in its active form or dormant forms in mammal. Specifically in animals and human. Although the present embodiments have been described with reference to specific example embodiments, it will be evident that various modifications and changes may be made to these embodiments without departing from the broader spirit and scope of the various embodiments. Accordingly, the specification and drawings are to be regarded in an illustrative rather than a restrictive sense.

What is claimed is:

1. A composition for treating all forms of a *Borrelia* sp simultaneously, comprising;
    a fatty acid, essential oil, plant extract, phenol, and terpenoid in a specific concentration individually, wherein the specific concentration is between 0.075 mg/ml-0.3 mg/ml for each of the ingredients in the composition wherein the fatty acid is a linoleic acid, the essential oil is at least one of a lemongrass oil, spearmint oil, clove oil, citral or cinnamon oil, the plant extract is at least one of a clove oil, cinnamon oil, citral, thyme or ginger, the phenol is an eugenol, the terpinoids are at least one of a carvone and citral.

2. The composition of claim 1, consists of 0.075 mg/ml each of the linoleic acid, clove oil, lemongrass oil, spearmint oil and/or cinnamon oil.

3. The composition of claim 1, consists of 0.075 mg/ml each of the linoleic acid, eugenol, citral, R-carvone and/or cinnamon oil.

4. The composition of claim 1, consists of 0.01 mg/ml each of the linoleic acid, clove oil and lemongrass oil.

5. The composition of claim 1, consists of 0.01 mg/ml each of the spearmint oil and/or cinnamon oil, clove oil and lemongrass oil.

6. The composition of claim 1, consists of 0.01 mg/ml each of the linoleic acid, eugenol and lemongrass oil.

7. The composition of claim 1, consists of 0.01 mg/ml each of the R-Carvone and/or cinnamon oil, eugenol and citral.

8. The composition of claim 1, consists of 0.01 mg/ml each of the linoleic acid, clove oil and spearmint oil and/or cinnamon oil.

9. The composition of claim 1, consists of 0.01 mg/ml each of the linoleic acid, clove oil and R-carvone and/or cinnamon oil.

10. The composition of claim 1, wherein all forms of the *Borrelia* sp is a spirochete, knob/rounded shape form and biofilm.

11. The composition of claim 1, wherein the *Borrelia* sp is one of a *Borrelia Burgdorferi* and *Borrelia Garinii*.

12. A composition for treating all forms of a *Borrelia* sp simultaneously, consisting a combination of a fatty acid is a linoleic acid, an essential oil is at least one of a lemongrass oil, spearmint oil, clove oil, citral or cinnamon oil, a plant extract is at least one of a clove oil, cinnamon oil, citral, thyme or ginger, a phenol is an eugenol, and a terpinoids are at least one of a carvone and citral, wherein the combination of all the above ingredients does not exceed 0.3 mg/ml.

13. The composition of claim 12, wherein all forms of the *Borrelia* sp is a spirochete, knob/rounded shape form and biofilm.

14. The composition of claim 12, wherein the *Borrelia* sp is one of a *Borrelia Burgdorferi* and *Borrelia Garinii*.

15. The composition of claim 12, further consists of 0.075 mg/ml each of the linoleic acid, clove oil, lemongrass oil, spearmint oil and/or cinnamon oil.

16. The composition of claim 12, further consists of 0.075 mg/ml each of the linoleic acid, eugenol, citral, R-carvone and/or cinnamon oil.

* * * * *